United States Patent
Benchikh et al.

(10) Patent No.: US 8,735,556 B2
(45) Date of Patent: May 27, 2014

(54) SENSITIVE AND GENERIC ANTIBODIES AND MULTIPLE APPLICATIONS

(75) Inventors: Elouard Benchikh, Crumlin (GB); Andrew Philip Lowry, Crumlin (GB); Ivan McConnell, Crumlin (GB); Peter Stephen Fitzgerald, Crumlin (GB)

(73) Assignee: Randox Laboratories Limited, Crumlin (GB)

( * ) Notice: Subject to any disclaimer, the term of this patent is extended or adjusted under 35 U.S.C. 154(b) by 0 days.

(21) Appl. No.: 13/525,784

(22) Filed: Jun. 18, 2012

(65) Prior Publication Data

US 2012/0322089 A1    Dec. 20, 2012

(30) Foreign Application Priority Data

Jun. 16, 2011 (GB) .................................. 1110164.9

(51) Int. Cl.
| | | |
|---|---|---|
| *C07K 1/04* | (2006.01) | |
| *G01N 33/532* | (2006.01) | |
| *C07K 16/44* | (2006.01) | |
| *G01N 33/94* | (2006.01) | |

(52) U.S. Cl.
CPC ............ *C07K 16/44* (2013.01); *G01N 33/9486* (2013.01); *Y01S 436/823* (2013.01); *G01N 33/532* (2013.01)
USPC .......................................... 530/403; 436/544

(58) Field of Classification Search
CPC . C07K 16/44; G01N 33/9486; G01N 33/532; Y10S 436/823
See application file for complete search history.

(56) References Cited

U.S. PATENT DOCUMENTS

| | | | |
|---|---|---|---|
| 5,688,944 A | * | 11/1997 | Wang .............................. 540/529 |
| 5,851,779 A | | 12/1998 | Wang |
| 6,803,040 B1 | | 10/2004 | Buechler et al. |
| 2012/0244546 A1 | * | 9/2012 | Yu et al. .......................... 435/7.1 |
| 2012/0244557 A1 | * | 9/2012 | Yu et al. ....................... 435/7.92 |

FOREIGN PATENT DOCUMENTS

| | | |
|---|---|---|
| EP | 0584854 | 1/1998 |
| EP | 0583820 | 3/2002 |
| EP | 1216994 | 12/2008 |

OTHER PUBLICATIONS

McMillin et al. Estimation of carbamazepine and carbamazepine-10,11-epoxide concentrations in plasma using mathematical equations generated with two carbamazepine immunoassays. Am. J. Clin. Pathol. 2010, vol. 133, pp. 728-736.*
Learmonth et al. Synthesis, anticonvulsant properties and pharmacokinetic profile of novel 10,11-dihydro-10-oxo-5H-dibenz/b,f/azepine-5-carboxamide derivatives. Eur. J. Med. Chem. 2001, vol. 36, pp. 227-236.*
Harrison et al. Hapten synthesis for pesticide immunoassay development. Immunoassays or Trace Chemical Analysis, ACS Symposium Series; American Chemical Society,Washington D.C. 1990, pp. 14-27.*
Bring et al. "Does Oxcarbazepine Warrant Therapeutic Drug Monitoring?" *Clin Pharmacokinet*, 47(12): pp. 767-778 (2008).
Bahlmann et al. "Monitoring Carbamazepine in Surface and Wastewaters by an Immunoassay Based on a Monoclonal Antibody" *Anal Bioanal Chem*, 395: 1809-1820 (2009).
Krasowski "Therapeutic Drug Monitoring of the Newer Anti-Epilepsy Medications" *Pharmaceuticals*, 3: 1909-1935 (2010).
"Test Definition: FCAR, Carbamazepine, Free and Total, S" *Mayo Clinic, Mayo Medical Laboratories* (2011).

* cited by examiner

*Primary Examiner* — Shafiqul Haq
(74) *Attorney, Agent, or Firm* — Cesari and McKenna, LLP

(57) ABSTRACT

The invention relates to the detection and quantification of carbamazepine drugs and their metabolites. The invention is underpinned by novel polyclonal antibodies with unique binding properties which enable immunoassay methods and kits for various applications.

2 Claims, 2 Drawing Sheets

SENSITIVE AND GENERIC ANTIBODIES AND MULTIPLE APPLICATIONS

RELATED APPLICATIONS

Figure 1:
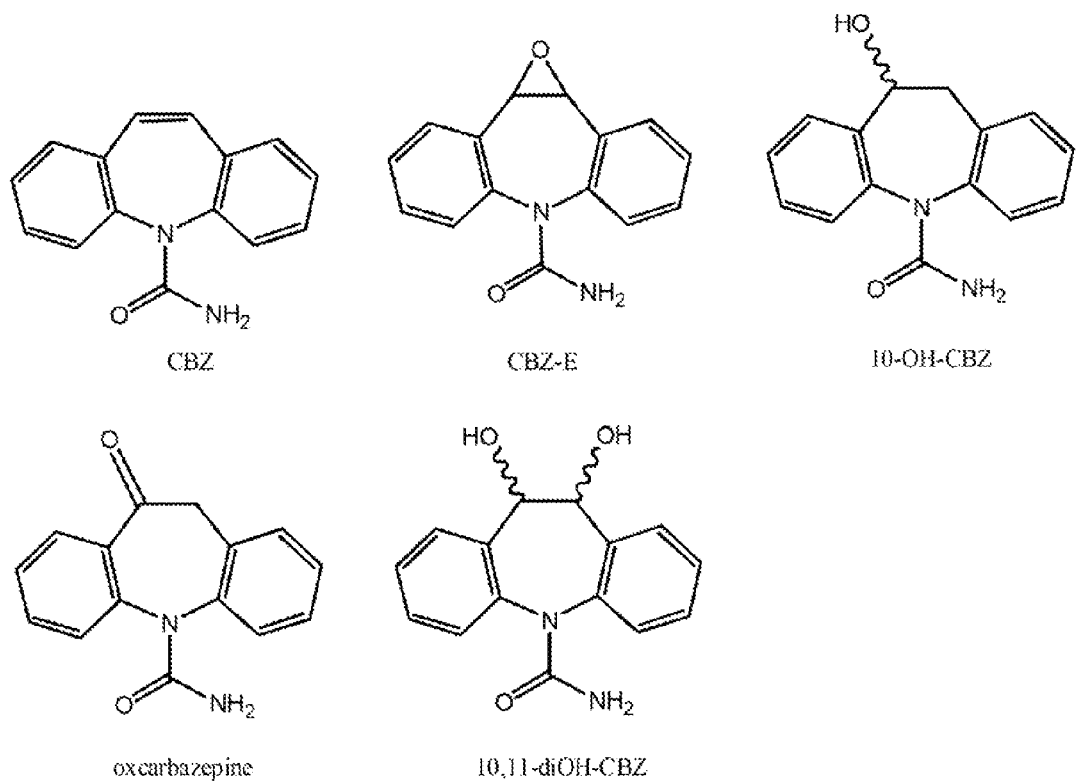

Under 35 U.S.C. 119, this application claims the benefit of the priority date of United Kingdom Application No. 1110164.9, filed Jun. 16, 2011, the content of which is herein incorporated by reference in its entirety.

FIELD OF THE INVENTION

The invention relates to the field of immunodiagnostics and describes anti-carbamazepine antibodies with surprising generic binding properties for use in methods and kits.

BACKGROUND TO THE INVENTION

The drug carbamazepine (CBZ) is widely prescribed for the treatment of various conditions including attention-deficit disorder, bipolar disorder, schizophrenia, and epilepsy. In patients, CBZ has a reported half-life of 18-65 hrs and is metabolised mainly to carbamazepine-10,11-epoxide (CBZ-E); 10,11-dihydro-10-hydroxycarbazepine (10-OH-CBZ); 10,11-dihydro-10,1-dihydroxycarbazepine (10,11-diOH-CBZ); and to minor amounts of the corresponding glucuronides. The major urinary excretory product is 10,11-diOH-CBZ (80%). The therapeutic range is reported as 2-10 µg/ml for total carbamazepine i.e. free and protein bound, and 0.5-3.6 µg/ml for free carbamazepine, the corresponding toxic values given as greater than 12.00 µg/ml and 4.00 µg/ml, respectively (Mayo Clinic, Mayo Medical Laboratories, 2011). Toxic concentrations can provoke drowsiness, headaches, affect motor function and in extreme cases are fatal. This narrow therapeutic index allied to inter-patient variability in drug-responsiveness requires that the blood concentration of CBZ and its main active metabolite CBZ-E be monitored in patients on CBZ therapy. The immunoassay is a common analytical test format used for the therapeutic drug monitoring (TDM) of patients on drugs such as CBZ and are based on antibodies that bind the target analyte(s). Several immunoassays/immunoassay components are described that bind carbamazepine and one or more metabolites at various concentrations e.g. EP 1216994, U.S. Pat. No. 5,851,779, EP0584854, EP0583820, U.S. Pat. No. 6,803,040. Several commercial immunoassay kits of varying specificity are available, many of which describe a TDM use for patients on carbamazepine therapy (Table 1). TDM applications based on immunoassays are best suited by antibodies that have high specificity for either the parent drug or an active metabolite to enable accurate measurements of its concentration, whereas toxicological applications do not necessarily have this specificity requirement.

Oxcarbazepine is a recent anti-epileptic drug that rapidly metabolises to 10-OH-CBZ and is considered a candidate for TDM (Bring and Ensom 2008; Krasowski 2010). An antibody that binds to oxcarbazepine/10-OH-CBZ could be used in an immunoassay for monitoring in vitro samples of patients undergoing oxcarbazepine drug therapy. Such an antibody could also be applied in an immunoassay for the TDM of other drugs of the carbamazepine family that produce 10-OH-CBZ as a metabolite. Immunoassays incorporating such antibodies could also have other applications, such as in toxicology. None of the immunoassays described in the prior art (including commercial assays described in Table I) have substantial cross-reactivity towards oxcarbazepine/10-OH-CBZ and are therefore unsuitable for such purposes.

The cross-reactivity profiles of the commercial assays displayed in Table I suggest immunogens used to raise the antibodies of the assays were derived through derivatisation at the carboxamide/1-position of a carbamazepine/carbamazepine-like hapten (pre-immunogenic, small molecule). The extent of consumption of pharmaceuticals has resulted in concerns over the levels of drugs and their metabolites in the aquatic environment, one of which is carbamazepine. Detection of pharmaceutical drugs such as carbamazepine in drinking water and environmental water bodies for their ecotoxicogical effects is desirable. A recently described CBZ immunoassay incorporating a monoclonal antibody detected CBZ and CBZ-E but had negligible cross-reactivity towards oxcarbazepine, 10-OH-CBZ and 10,11-di-OH-CBZ (Bahlmann et al. 2009). It is probable the amount of carbamazepine in water bodies was underestimated by this immunoassay as the antibody showed negligible binding to the major urinary metabolite of carbamazepine, 10,11-di-OH-CBZ. Antibodies of current carbamazepine immunoassays do not cross-react with 10,11-di-OH-CBZ and would therefore underestimate levels of carbamazepine drug in the aquatic environment. A preferred immunoassay would find application in the TDM of carbamazepine, of newer carbamazepine-based drugs and for the monitoring of carbamazepine-based drugs in the environment. It is evident that current immunoassays, in which the assay antibodies have high affinity for CBZ and CBZ-E, do not possess this broad applicability.

BIBLIOGRAPHY

Bring P. and Ensom M. H. H. 2008. *Clin. Pharmac.*, 47: 767-778.
Bahlmann A. et al. 2009. *Anal. Bioanal. Chem.*, 395: 1809-1820.
Krasowski M. D. 2010. *Pharmacecuticals*, 3: 1909-1935.
Mayo Clinic, http://www.mayomedicallaboratories.com/test-catalog/print.php?unit_code=81770 at 25 Mar. 2011.

DRAWINGS

Figure 2:
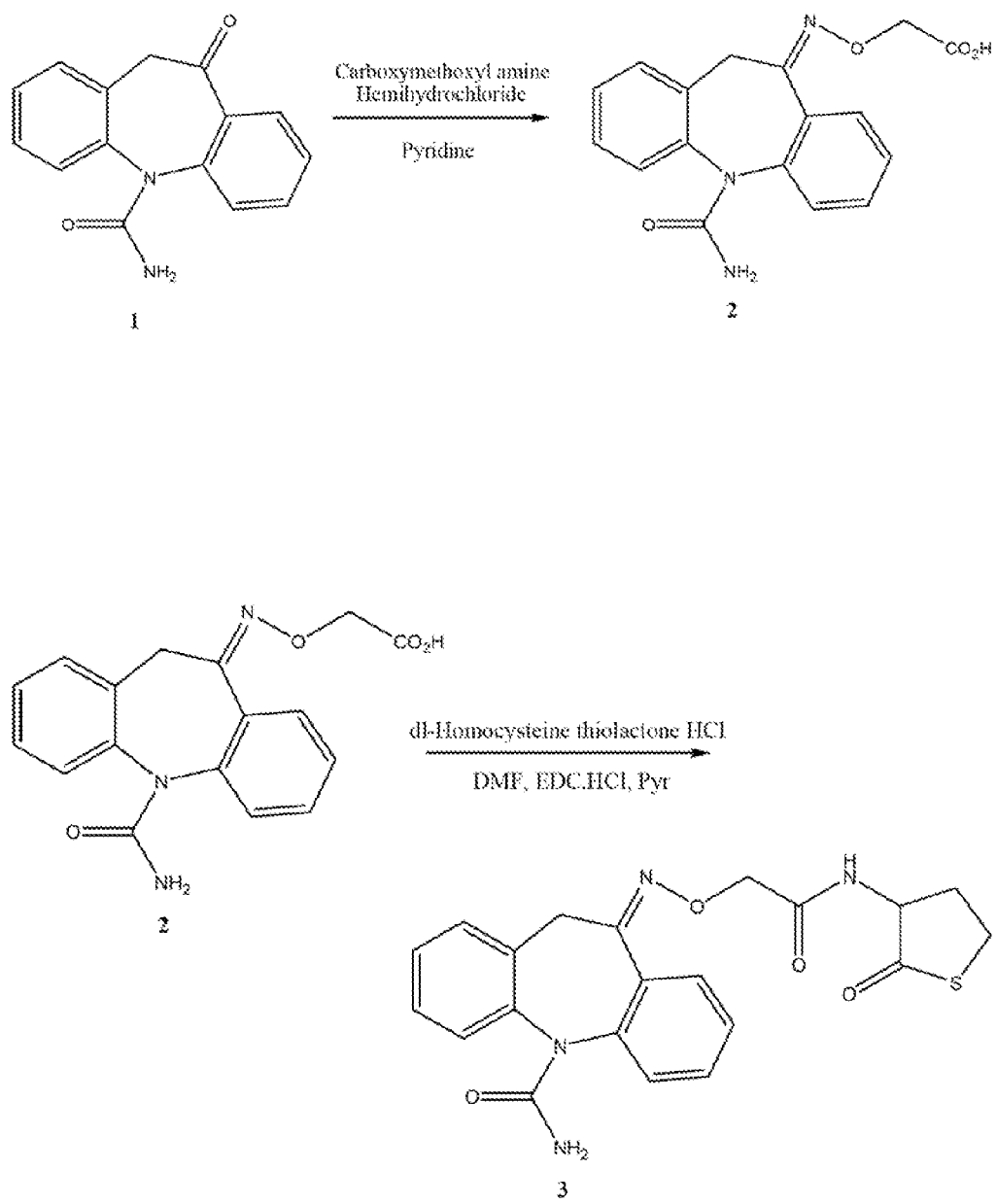

FIG. 1 Structures of carbamazepine and major metabolites
FIG. 2 Preparation of Haptens A and B

TABLE 1

Commercially available carbamazepine immunoassays*

| Supplier | Analyzer/Method | Cross-reactivity | |
|---|---|---|---|
| Abbott Diagnostics | Axsym | CBZ-E | ≤83.0% |
| | | Desipramine | ≤540.0% |
| Roche Diagnostics | Online TDM** | CBZ-E | 14.0% |
| | | 10-OH-CBZ | 1.2% |
| | | Oxcarbazepine | 1.0% |
| Siemens | ADVIA | CBZ-E | 21.8% |
| | | Amitryptyline | 5.2% |
| | | Nortryptyline | 5.2% |
| Beckman Coulter (BC) | BC analyzers | CBZ-E | 7.4% |
| | | Amitryptyline | 18.6% |
| | | Nortryptyline | 17.2% |
| | | Phenothiazine | 8.6% |
| | | Imipramine | 5.6% |
| | | Diazepam | 4.8% |

*Data taken from manufacturers' data-sheets or FDA 512(k)
**At 6 µg/ml of carbamazepine

SUMMARY OF THE INVENTION

The invention describes immunogens used in the production of novel polyclonal antibodies with unique binding properties which overcome the application limitations of currently described immunoassays by enabling methods and kits for the detection and quantification of oxcarbazepine/10,11-dihydro-10-hydroxycarbazepine in in vitro patient samples and more accurate enviroaquatic immunoassay testing of the level of drugs from the carbamazepine family, including 10,11-dihydro-10,11-dihydroxycarbazepine. Furthermore, the generic cross-reactivity of the antibodies enables a standard carbamazepine/carbamazepine-10,11-epoxide immunoassay to be effected.

According to a first aspect of the present invention, there is provided an immunogen having the general structure (I):

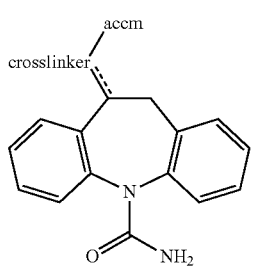

(I)

Optionally, the accm is selected from bovine serum albumin (BSA), egg ovalbumin, bovine gamma globulin, bovine thyroglobulin (BTG), keyhole limpet haemocyanin (KLH), synthetic poly(amino acids) having a sufficient number of available amino groups, lysine, and synthetic or natural polymeric materials bearing reactive functional groups. Further optionally, the accm is bovine thyroglobulin (BTG).

Optionally, the crosslinker has the general structure (II):

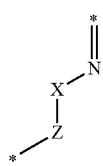

(II)

wherein, X is a short chain alkyl, alkenyl, or alkynyl group, which can be branched or unbranched, substituted or unsubstituted, linear or cyclic; and Z is a functional group selected from a carbonyl group and an amino group.

Optionally, X is a $C_{1-10}$ chain alkyl, alkenyl, or alkynyl group, which can be branched or unbranched, substituted or unsubstituted, linear or cyclic. Further optionally, X is a $C_{2-6}$ chain alkyl, alkenyl, or alkynyl group, which can be branched or unbranched, substituted or unsubstituted, linear or cyclic.

Optionally or alternatively, X is a short chain alkoxyl, alkenoxyl, or alkynoxyl group, which can be branched or unbranched, substituted or unsubstituted, linear or cyclic; and Z is a functional group selected from a carbonyl group and an amino group.

Optionally, X is a $C_{1-10}$ chain alkoxyl, alkenoxyl, or alkynoxyl group, which can be branched or unbranched, substituted or unsubstituted, linear or cyclic. Further optionally, X is a $C_{2-6}$ chain alkoxyl, alkenoxyl, or alkynoxyl group, which can be branched or unbranched, substituted or unsubstituted, linear or cyclic.

Optionally, X is —O—$CH_2$— and Z is a carbonyl group.

Optionally or alternatively, the crosslinker has the general structure (III):

(III)

wherein, Y is a short chain alkyl, alkenyl, or alkynyl group, which can be branched or unbranched, substituted or unsubstituted, linear or cyclic; and Z is a functional group selected from a carbonyl group and an amino group.

Optionally, Y is a $C_{1-10}$ chain alkyl, alkenyl, or alkynyl group, which can be branched or unbranched, substituted or unsubstituted, linear or cyclic. Further optionally, Y is a $C_{2-6}$ chain alkyl, alkenyl, or alkynyl group, which can be branched or unbranched, substituted or unsubstituted, linear or cyclic.

According to a second aspect of the present invention, there is provided an antibody derivable from the immunogen of the first aspect of the present invention.

Optionally, the antibody is a monoclonal antibody. Alternatively, the antibody is a polyclonal antibody. Further alternatively, the antibody is a fragment, optionally a single chain variable fragment.

Optionally, the antibody according to the second aspect of the present invention has an $IC_{50}$ selected from one or more of about 2 ng/ml for carbamazepine, of about 3 ng/ml for carbamazepine-10,11-epoxide, of about 3 ng/ml for 10,11-dihydro-10-hydroxycarbamazepine, of about 1 ng/ml for oxcarbazepine, and of about 15 ng/ml for 10,11-dihydro-10,11-dihydroxycarbamazepine.

Further optionally, the antibody according to the second aspect of the present invention has an $IC_{50}$ selected from one or more of at least 2.135 ng/ml for carbamazepine, of at least 3.125 ng/ml for carbamazepine-10,11-epoxide, of at least 3.167 ng/ml for 10,11-dihydro-10-hydroxycarbamazepine, of at least 0.714 ng/ml for oxcarbazepine, and of at least 15.269 ng/ml for 10,11-dihydro-10,11-dihydroxycarbamazepine.

Optionally, the antibody according to the second aspect of the present invention is capable of binding to at least one epitope of an analyte selected from carbamazepine, carbamazepine-10,11-epoxide, 10,11-dihydro-10-hydroxycarbamazepine, oxcarbazepine and 10,11-dihydro-10,11-dihydroxycarbamazepine. Further optionally, the antibody has an $IC_{50}$ of about 2 ng/ml for carbamazepine, of about 3 ng/ml for carbamazepine-10,11-epoxide, of about 3 ng/ml for 10,11-dihydro-10-hydroxycarbamazepine, of about 1 ng/ml for oxcarbazepine, and of about 15 ng/ml for 10,11-dihydro-10,11-dihydroxycarbamazepine.

According to a third aspect of the present invention, there is provided a method of preparing an antibody capable of binding to at least one epitope of an analyte selected from carbamazepine, carbamazepine-10,11-epoxide, 10,11-dihydro-10-hydroxycarbamazepine, oxcarbazepine and 10,11-dihydro-10,11-dihydroxycarbamazepine; the method comprising raising the antibody against the immunogen of the first aspect of the present invention.

Optionally, the raising step comprises preparing an antiserum. Further optionally, the raising step comprises preparing an antiserum by immunizing an animal. Still further optionally, the raising step comprises preparing an antiserum by immunizing an animal and isolating antibodies from the animal.

According to a fourth aspect of the present invention, there is provided an antibody derivable from the method according to the third aspect of the present invention.

Optionally, the antibody is a monoclonal antibody. Alternatively, the antibody is a polyclonal antibody. Further alternatively, the antibody is a fragment, optionally a single chain variable fragment.

Optionally, the antibody according to the fourth aspect of the present invention has an $IC_{50}$ selected from one or more of about 2 ng/ml for carbamazepine, of about 3 ng/ml for carbamazepine-10,11-epoxide, of about 3 ng/ml for 10,11-dihydro-10-hydroxycarbamazepine, of about 1 ng/ml for oxcarbazepine, and of about 15 ng/ml for 10,11-dihydro-10,11-dihydroxycarbamazepine.

Further optionally, the antibody according to the fourth aspect of the present invention has an $IC_{50}$ selected from one or more of at least 2.135 ng/ml for carbamazepine, of at least 3.125 ng/ml for carbamazepine-10,11-epoxide, of at least 3.167 ng/ml for 10,11-dihydro-10-hydroxycarbamazepine, of at least 0.714 ng/ml for oxcarbazepine, and of at least 15.269 ng/ml for 10,11-dihydro-10,11-dihydroxycarbamazepine.

Optionally, the antibody according to the fourth aspect of the present invention is capable of binding to at least one epitope of an analyte selected from carbamazepine, carbamazepine-10,11-epoxide, 10,11-dihydro-10-hydroxycarbamazepine, oxcarbazepine and 10,11-dihydro-10,11-dihydroxycarbamazepine. Further optionally, the antibody has an $IC_{50}$ of about 2 ng/ml for carbamazepine, of about 3 ng/ml for carbamazepine-10,11-epoxide, of about 3 ng/ml for 10,11-dihydro-10-hydroxycarbamazepine, of about 1 ng/ml for oxcarbazepine, and of about 15 ng/ml for 10,11-dihydro-10,11-dihydroxycarbamazepine.

According to a fifth aspect of the present invention, there is provided a method of detecting or determining one or more of carbamazepine, carbamazepine-10,11-epoxide, 10,11-dihydro-10-hydroxycarbamazepine, oxcarbazepine, and 10,11-dihydro-10,11-dihydroxycarbamazepine; the method comprising contacting a sample with the antibody according to the second aspect of the present invention or the antibody according to the fourth aspect of the present invention; detecting or determining the quantity of the antibody; and attributing the presence or amount of the antibody to the presence or amount of one or more of carbamazepine, carbamazepine-10,11-epoxide, 10,11-dihydro-10-hydroxycarbamazepine, oxcarbazepine, and 10,11-dihydro-10,11-dihydroxycarbamazepine in the sample.

Optionally, the method comprises the further step of detecting or determining the quantity of a label or detecting agent capable of binding to the antibody according to the second aspect of the present invention or the antibody according to the fourth aspect of the present invention for detecting or determining the quantity of the antibody.

Also disclosed is an assay for detecting or determining one or more of carbamazepine, carbamazepine-10,11-epoxide, 10,11-dihydro-10-hydroxycarbamazepine, oxcarbazepine, and 10,11-dihydro-10,11-dihydroxycarbamazepine; the assay comprising the antibody according to the second aspect of the present invention or the antibody according to the fourth aspect of the present invention; and means for detecting or determining the quantity of the antibody to detect or determine the presence or amount of one or more of carbamazepine, carbamazepine-10,11-epoxide, 10,11-dihydro-10-hydroxycarbamazepine, oxcarbazepine, and 10,11-dihydro-10,11-dihydroxycarbamazepine in the sample.

Optionally, the assay further comprises a solid support to which the antibody is conjugated.

Also disclosed is a kit for detecting or determining one or more of carbamazepine, carbamazepine-10,11-epoxide, 10,11-dihydro-10-hydroxycarbamazepine, oxcarbazepine, and 10,11-dihydro-10,11-dihydroxycarbamazepine; the kit comprising the antibody according to the second aspect of the present invention or the antibody according to the fourth aspect of the present invention.

Optionally, the kit further comprises instruction for use.

DETAILED DESCRIPTION OF THE INVENTION

The invention provides an immunogen of structure

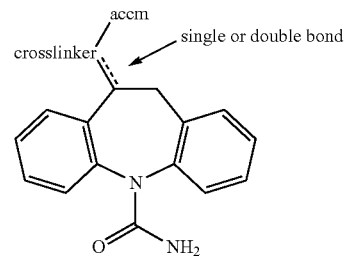

in which the crosslinker is preferably

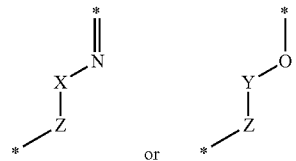

in which X is a substituted or unsubstituted alkyl, alkylene or arylene group or an oxygen attached to a substituted or unsubstituted alkyl, alkylene or arylene group and Y is a substituted or unsubstituted alkyl, alkylene or arylene group; the alkyl or alkylene groups of X and Y are preferably $C_{1-10}$, most preferably $C_{1-6}$, Z is either carbonyl or amino and is attached to the accm. The preferred crosslinker is where X is —O—$CH_2$— and Z is carbonyl, the methylene group of X being attached to Z. In the field of antibody development it is generally considered that the optimum length of the linking group joining the analyte to be detected to the accm (straight chain length and not including hydrogen atoms) is about 1-10 atoms, more usually about 1-6 atoms. For the purpose of the invention the crosslinker is the chain of atoms linking position 10 of the tricyclic ring to the accm. The accm is an antigenicity conferring carrier material and is any material that makes all or part of the carbamazepine moiety susceptible to antibody recognition and binding. For example the accm can be a protein, a protein fragment, a synthetic polypeptide or a semi-synthetic polypeptide. The accm is preferably bovine thyroglubulin (BTG). The invention also describes sensitive antibodies with novel generic cross-reactivity enabling for the first time a multi-application utility i.e to be used in TDM, toxicology and environmental detection.

Thus, another aspect of the invention is antibodies that bind to an epitope of carbamazepine, carbamazepine-10,11-epoxide, 10,11-dihydro-10-hydroxycarbamazepine, oxcarbazepine and 10,11-dihydro-10,11-dihydroxycarbamazepine characterized in having sufficient sensitivity, optionally sufficient sensitivity based on the IC50 as described herein below; to be of use in toxicological and environmental applications. The ability of the antibodies to recognise CBZ and CBZ-E enables a TDM test for patients on CBZ therapy; oxcarbazepine and 10-OH-CBZ recognition enables a TDM test for patients on oxcarbazepine; 10,11-di-OH-CBZ recognition enables an enviroaquatic monitoring kit; also, the high sensitivity of the antibodies to oxcarbazepine, CBZ and 10-OH-CBZ enables the use of the antibodies in toxicological applications. The skilled person is aware that antibody generic cross-reactivity does not necessarily provide for an antibody fit for industrial application unless the associated sensitivity is within a range that can be of practical use. A common measure of antibody sensitivity for immunoassays is the $IC_{50}$. It is also recognized that for immunoassays that utilize a competitive format, the exact $IC_{50}$ value varies slightly depending on the nature of the conjugate used to compete with the analyte in the sample.

A further aspect of the invention is antibodies that have an $IC_{50}$ of about 2 ng/ml for carbamazepine, of about 3 ng/ml for carbamazepine-10,11-epoxide, of about 3 ng/ml for 10,11-dihydro-10-hydroxycarbamazepine, of about 1 ng/ml for oxcarbazepine and of about 15 ng/ml for 10,11-dihydro-10, 11-dihydroxycarbamazepine.

A still further aspect of the invention is antibodies that have an $IC_{50}$ of at least 2.135 ng/ml for carbamazepine, of at least 3.125 ng/ml for carbamazepine-10,11-epoxide, of at least 3.167 ng/ml for 10,11-dihydro-10-hydroxycarbamazepine, of at least 0.714 ng/ml for oxcarbazepine and of at least 15.269 ng/ml for 10,11-dihydro-10,11-dihydroxycarbamazepine. It is known to the skilled person that by varying the antibody concentration through dilution, that the $IC_{50}$ values can be adjusted depending upon the application. As stated previously, TDM of CBZ is generally implemented at the µg/ml concentration.

Another aspect of the invention is the previously described antibodies raised from one or more of the previously described immunogens.

The antibodies of the invention are preferably polyclonal, but can be synthetically and/or genetically engineered derivatives such as monoclonal antibodies or single chain variable fragments (scFvs).

The invention also provides methods of detecting or determining one or more of carbamazepine carbamazepine-10,11-epoxide, 10,11-dihydro-10-hydroxycarbamazepine, oxcarbazepine and 10,11-dihydro-10,11-dihydroxycarbamazepine in an in vitro sample of an individual or an environmental sample comprising; contacting the sample with one or more detecting agents and one or more antibodies of the invention; detecting, or determining the quantity of, the one or more detecting agents; and deducing from calibrators, the presence of or amount of one or more of carbamazepine, carbamazepine-10,11-epoxide, 10,11-dihydro-10-hydroxycarbamazepine, oxcarbazepine, and 10,11-dihydro-10,11-dihydroxycarbamazepine in the sample.

'Detecting' means qualitatively analyzing for the presence or absence of a substance, 'determining' means quantitatively analyzing for the amount of a substance. The detecting agent is a small molecule (generally of similar structure to a molecule to be detected), conjugated to a labelling/detecting agent that is able to bind to one of the antibodies of the invention. The labelling agent is selected from an enzyme, a luminescent substance, a radioactive substance, or a mixture thereof. Preferably, the labelling agent is an enzyme, preferably a peroxidase, most preferably horseradish peroxidase (HRP). Alternatively, or additionally, the luminescent substance may be a bioluminescent, chemiluminescent or fluorescent material. For the purposes of the invention, the patient sample to be used for in vitro analysis can be hair or a peripheral biological fluid but is preferably whole blood, serum, plasma, or urine. If the history of the sample is unknown, e.g. if it is a blood or urine sample taken from an unconscious patient, the method will be semi-quantitative i.e. several molecules could be detected and a 'standard equivalent' amount quantified. If the history of the sample is known, e.g. if it is a urine sample from an individual on oxcarbazepine therapy, the method can be classed as essentially quantitative as 10-OH-CBZ will be detected, the unchanged parent representing less than 1% of excreted product.

A further aspect of the invention is a kit for detecting or determining one or more of carbamazepine, carbamazepine-10,11-epoxide, 10,11-dihydro-10-hydroxycarbamazepine, oxcarbazepine and 10,11-dihydro-10,11-dihydroxycarbamazepine comprising one or more antibodies of the invention. Optionally, the kits may contain one or more detecting agents and one or more calibrators.

Antibodies, methods and kits of the invention can be used in various applications such as TDM, toxicology and for more accurate environmental monitoring of these drugs.

GENERAL METHODS, EXAMPLES AND RESULTS

Preparation of Haptens, Immunogens and Detecting Agents

Although the target small molecules provide structural epitopes, they are not in themselves immunogenic and therefore need to be conjugated to carrier materials, which will elicit an immunogenic response when administered to a host animal. Appropriate carrier materials commonly contain poly (amino acid) segments and include polypeptides, proteins and protein fragments. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. The coupling chemistry used to prepare an immunogen from a hapten and carrier protein is an important consideration for the successful production and the correct specificity of the resultant antibodies. The choice of cross-linking methodology is governed by the functional groups present on both the carrier and the hapten as well as the orientation of the hapten desired for appropriate presentation to the immune system. Also, carbohydrates, yeasts or polysaccharides may be conjugated to the hapten to produce an immunogen. The haptens can also be coupled; the carbodiimide first reacts with available carboxylic groups of the haptens to form a highly active O-acylisourea intermediate. The activated carboxylic group the react with the primary amine to form an amide bond, with the release of the EDC mediator as a soluble isourea derivative to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Immunogen formation for the invention described herein involves conventional conjugation chemistry Bioconjugation Techniques" by Greg T. Hermanson, Academic Press, pages 419-455 and "Bioconjugation" by Mohammed Aslam and Alastair Dent, ISBN 1-56159-161-0 (1998) pages 364-482. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Preparation of Antisera

In order to generate polyclonal antisera, 2 mg of an immunogen of the present invention is prepared in PBS (0.5 ml), mixed at a ratio of 50% Immunogen in PBS to 50% Freund's Complete (0.5 ml) adjuvant (Sigma, Product Number-F5881) and emulsified by repeatedly passing the mixture through a tip on the end of a 1 ml syringe, until it reaches the required semi-solid consistency. 1 ml of the mixture is injected into a host animal, such as rabbit, sheep, mouse, guinea pig or horse. Sheep are the preferred host animal. Further injections (boosts) are administered (1 mg of immunogen is prepared in PBS and mixed at a ratio of 50% Immunogen in PBS/50% Freunds Incomplete adjuvant, Sigma, Product Number—F5506) on a monthly basis until the required titre is achieved. Serum is sampled for evaluation of the antibody titre. Briefly, blood is collected by applying pressure to the exposed jugular vein and inserting a clean 14 gauge hypodermic needle to remove 500 ml of blood per sheep, under gravity. The blood is stored at 37° C. for a minimum of 1 hour before the clots are separated from the side of the centrifuge bottles using disposable 1 ml pipettes (ringing). The samples are stored at 4° C. overnight.

Samples are then centrifuged at 4200 rpm for 30 minutes at 4° C. The serum is poured off and centrifuged again, at 10,000 rpm for 15 minutes at 4° C., before being aliquoted and stored at <−20° C.

The Immunoglobulin (Ig) fraction is extracted from the antisera via caprylic acid/ammonium sulphate precipitation of immunoglobulin.

The antibody titre is evaluated by coating a microtitre plate (Thermo Fisher Scientific NUNC, 468667) with antibody (125 µl/well) in coating buffer (10 mM Tris pH 8.5) at 37° C. for 2 hours. The plate is then washed 4 times over 10 minutes with working strength TBST. 50 µl of sample/standard (Carbamazepine, Sigma C4024) is added to the appropriate wells in triplicate, followed by 75 µl of hapten-HRP conjugate and incubated at 25° C. for 1 hour. The plate is then washed and 125 µl of TMB (Randox, 4380-15) added to each well and left at room temperature for 20 mins in the dark. The reaction is stopped using 125 µl of 0.2M sulphuric acid. The absorbances are read at 450 nm with an ELISA microplate reader (BIO-TEK Instruments, Elx800) and the means calculated. Antibody sensitivity can then be determined.

When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Various purification steps are available if required, including Immunoglobulin Precipitation (as described above), Antigen-specific affinity purification, Size-exclusion chromatography and Ion Exchange Chromatography.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal antibodies.

This can be carried out using an ELISA based format as described above for measuring antibody titre or as a Biochip based format. Details of how the antibodies are fixed to the Biochip are described in FitzGerald, S. P. el al, Clin. Chem. 51(7); 1165-1176; 2005.

The signal emitted in the immunoassay is proportionate to the amount of detecting agent bound to the antibodies which in turn is inversely proportionate to the analyte concentration. The signal can be detected or quantified by comparison with a calibrator, as described in Example 7 herein below.

EXAMPLES

Example 1

Synthesis of oxcarbazepine-7-carboxymethyloxime 2 (Hapten-A)

To a solution of oxcarbazepine 1 (2.52 g, 10 mM) in dry pyridine (50 ml) under nitrogen was added carboxymethoxylamine hemihydrochloride (1.31 g, 12 mM) and the mixture was stirred overnight at room temperature. The mixture began cloudy but turned clear yellow after few hours. The solvent was removed under vacuum and the residue obtained purified by flash chromatography on silica gel using 10% methanol/90% chloroform to give 2.3 g of the product as a foam. The product was then triturated by ethyl acetate/hexane (1/1) the white solid formed was filtered and dried to give 2 g of oxcarbazepine-7-carboxymethyloxime 2 (Hapten-A). M. P. 205° C. (dec). NMR $^{13}$C (CD$_3$OD)(δ: ppm): 171.21, 156.17, 154.49, 143.45, 141.16, 134.25, 130.77, 130.66, 130.57, 129.70, 128.64, 128.58, 128.31, 128.06, 127.6, 71.09 and 32.17.

Example 2

Synthesis of oxcarbazepine-7-carboxymethyloxime homocysteine thiolactone 3 (Hapten-B)

To a solution under nitrogen of oxcarbazepine-7-carboxymethyloxime 2 (Hapten-A) (1 g, 3.07 mM) in dry pyridine (25 ml) was added homocysteine thiolactone hydrochloride (568 mg, 3.7 mM) and EDC hydrochloride (710 mg, 3.7 mM) and the mixture was stirred overnight at room temperature, TLC indicated reaction to be complete. Pyridine was removed under vacuum and the residue obtained purified by flash chromatography on silica gel using 15% methanol/85% chloroform to afford 885 mg of the pure oxcarbazepine-7-carboxymethyloxime homocysteine thiolactone 3 (Hapten-B) as an off-white foamy solid.

NMR $^{13}$C (CD$_3$OD))(δ: ppm): 205.53, 170.56, 156.62, 142.55, 131.37, 131.19, 130.88, 129.33, 129.11, 128.42, 73.81, 60.78, 59.44, 32.10, 28.91, 21.43.

Example 3

Conjugation of Hapten-A to BSA (Immunogen-1)

To a solution of oxcarbazepine-7-carboxymethyloxime 2 (Hapten-A) (38.73 mg, 0.112 mmol) in DMF (1.0 ml) was added N,N-dicyclohexylcarbodiimide (DCC) (25.35 mg, 0.123 mmol) and N-hydroxysuccinimide (14.13 mg, 0.123 mmol) and the mixture was stirred at room temperature overnight. The dicyclohexylurea formed was removed by filtration and the solution was added dropwise to a solution of BSA (150 mg, 2.3 μmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried. MALDI results showed 24.99 molecule of hapten-A had been conjugated to one molecule of BSA.

Example 4

Conjugation of Hapten-A to BTG (Immunogen-II)

To a solution of oxcarbazepine-7-carboxymethyloxime 2 (Hapten-A) (43.91 mg, 0.135 mmol) in DMF (1.0 ml) was added N,N-dicyclohexylcarbodiimide (DCC) (30.7 mg, 0.149 mmol) and N-hydroxysuccinimide (17.13 mg, 0.149 mmol) and the mixture was stirred at room temperature overnight. The dicyclohexylurea formed was removed by filtration and the solution was added dropwise to a solution of BTG (150 mg), in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried.

Example 5

Conjugation of Hapten-A to HRP

EDC hydrochloride (10 mg) was dissolved in water (0.5 ml) and immediately added to a solution of oxcarbazepine-7-Carboxymethyloxime 2 (Hapten-A) (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Example 6

Conjugation of Hapten-B to maleimide modified HRP

Hapten-B (2 mg) was dissolved in a mixture of DMF/water (100 μl) and to this solution was added potassium hydroxide (2M) (10 μl □ □ □ The mixture was allowed to stand for 10 minutes. Phosphate buffer (100□μl) was added to quench the reaction and the pH was adjusted to 7 by the addition of 0.1M HCl. This solution was added dropwise to maleimide modified HRP (20 mg) dissolved in phosphate buffer (1 ml) and the solution stirred at 4° C. overnight (protected from light). Excess hapten was removed with double PD-10 columns (Pharmacia) in series, pre-equilibrated with PBS at pH 7.2. The hapten-HRP conjugate was then dialysed with 10 L of PBS at pH 7.2 at 4° C.

Example 7

Development of a Competitive ELISA

Carbamazepine was conjugated to bovine thyroglobulin (BTG), using the same techniques as described above for Hapten A. The immunogenic mixture (1 ml) was administered to adult sheep on a monthly basis to provide target-specific polyclonal antisera. IgG was extracted from the antisera via caprylic acid/ammonium sulphate precipitation of immunoglobulin. A microtitre plate (Thermo Fisher Scientific NUNC, 468667) was coated with antibody (125 μl/well) in coating buffer (10 mM Tris pH 8.5) at 37° C. for 2 hours. The plate was then washed 4 times over 10 minutes with working strength TBST. 50 μl of sample/standard (carbamazepine, Sigma C4024; carbamazepine-10,11-epoxide, TRC C175850; 10,11-dihydro-10-hydroxycarbamazepine, TRC D449135; rac trans-10,11-dihydro-10,11-dihydroxy carbamazepine, TRC D449040; oxcarbazepine, TRC 0869250; imipramine, Sigma 17379 and amitriptyline, Sigma A8404) was added to the appropriate wells in triplicate, followed by 75 μl of hapten-HRP conjugate and incubated at 25° C. for 1 hour. The plate was then washed and 125 μl of TMB (Randox, 4380-15) was added to each well and left at room temperature for 20 mins in the dark. The reaction was stopped using 125 μl of 0.2M sulphuric acid. The absorbances were read at 450 nm with an ELISA microplate reader (BIO-TEK Instruments, Elx800) and the means calculated. Antibody specificity and sensitivity were then determined.

RESULTS

Employing each series of standards, calibration curves were generated and these were used to determine the specificity of the immunoassay for the carbamazepine, oxcarbazepine, metabolites and structurally-related molecules. The results of this study are presented in Table 2, cross-reactivity being calculated according to the following formula:

$$\% \text{ CR} = IC_{50, \text{ carbamazepine}}/IC_{50, CR} \times 100$$

Where % CR is the percentage cross-reactivity, $IC_{50}$ carbamazepine is the concentration of carbamazepine that causes 50% displacement of signal and $IC_{50, CR}$ is the concentration of carbamazepine/metabolites/structurally-related molecules that causes 50% displacement of signal. The results show an antibody of high individual-molecule sensitivity and generic cross-reactivity, enabling it to be used in a diverse range of applications.

TABLE 2

Antibody characterisation using antiserum raised to Immunogen II and detecting agent derived from Hapten-A in a competitive assay format (CR based on 100% for carbamazepine)

| Analyte | $IC_{50}$ ng/ml | % Cross-reactivity |
| --- | --- | --- |
| CBZ | 2.135 | 100.00 |
| CBZ-E | 3.125 | 68.30 |
| 10-OH-CBZ | 3.167 | 67.40 |
| 10,11-diOH-CBZ | 15.269 | 14.00 |
| Oxcarbazepine | 0.714 | 299.00 |
| Amitriptyline | >>200 | <<1.10 |
| Imipramine | >>200 | <<1.10 |

The invention claimed is:

1. An immunogen having the general structure (I):

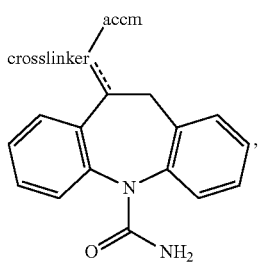

(I)

wherein accm is an antigenicity conferring carrier material selected from the group consisting of a protein, a protein fragment, a synthetic polypeptide, and a semi-synthetic polypeptide, and the crosslinker has the general structure (II):

(II)

where X is —O—CH$_2$— and Z is a carbonyl group, Z being bonded to the accm.

2. The immunogen of claim 1, wherein the accm is bovine serum albumin (BSA), egg ovalbumin, bovine gamma globulin, bovine thyroglobulin (BTG), keyhole limpet haemocyanin (KLH), synthetic poly(amino acids) having a sufficient number of available amino groups, lysine, or synthetic or natural polymeric materials bearing reactive functional groups.

* * * * *